US011865045B2

(12) United States Patent
Junger et al.

(10) Patent No.: US 11,865,045 B2
(45) Date of Patent: Jan. 9, 2024

(54) SYSTEMS AND METHODS FOR PERFORMING AN INTRAOCULAR PROCEDURE FOR TREATING AN EYE CONDITION

(71) Applicant: Elios Vision, Inc., Los Angeles, CA (US)

(72) Inventors: Johannes Junger, Gilching (DE); Markus Enders, Munich (DE)

(73) Assignee: Elios Vision, Inc., Los Angeles, CA (US)

( * ) Notice: Subject to any disclaimer, the term of this patent is extended or adjusted under 35 U.S.C. 154(b) by 0 days.

(21) Appl. No.: 17/971,102

(22) Filed: Oct. 21, 2022

(65) Prior Publication Data
US 2023/0122205 A1 Apr. 20, 2023

Related U.S. Application Data

(63) Continuation of application No. 17/400,191, filed on Aug. 12, 2021, now Pat. No. 11,529,260, which is a
(Continued)

(51) Int. Cl.
A61F 9/008 (2006.01)
H01S 3/225 (2006.01)
(Continued)

(52) U.S. Cl.
CPC ........ A61F 9/00836 (2013.01); A61F 9/0084 (2013.01); H01S 3/10069 (2013.01);
(Continued)

(58) Field of Classification Search
CPC ................ A61F 9/00836; A61F 9/0084; A61F 9/00802; A61F 2009/00855; A61F 2009/00865; A61F 2009/00891; A61F 2009/00868; H01S 3/10069; H01S 3/1305; H01S 3/2253; H01S 3/225; H01S 3/0014; H01S 3/10038
See application file for complete search history.

(56) References Cited

U.S. PATENT DOCUMENTS 4,607,622 A 8/1986 Fritch et al.
4,846,172 A 7/1989 Berlin
(Continued)

FOREIGN PATENT DOCUMENTS

DE 19920615 A1 12/2000
DE 10023176 A1 11/2001
(Continued)

OTHER PUBLICATIONS

Dietlein et al., "Erbium: YAG Laser Trabecular Ablation (LTA) in the Surgical Treatment of Glaucoma", Lasers in Surgery and Medicine, Jan. 6, 1999, vol. 23, pp. 104-110.
(Continued)

Primary Examiner — Ankit D Tejani
Assistant Examiner — Joshua Brendon Solomon
(74) Attorney, Agent, or Firm — Greenberg Traurig, LLP; David J. Dykeman; Roman Fayerberg

(57) ABSTRACT

The invention provides an excimer laser system including a means for calibrating laser output to compensate for increased variation in laser optical fibers.

20 Claims, 6 Drawing Sheets

Related U.S. Application Data continuation of application No. 16/389,359, filed on Apr. 19, 2019, now Pat. No. 11,103,382.

(51) Int. Cl.
*H01S 3/13* (2006.01)
*H01S 3/10* (2006.01)

(52) U.S. Cl.
CPC .......... *H01S 3/1305* (2013.01); *H01S 3/2253* (2013.01); *A61F 2009/00855* (2013.01); *A61F 2009/00865* (2013.01); *A61F 2009/00891* (2013.01)

(56) References Cited

U.S. PATENT DOCUMENTS

| | | | |
|---|---|---|---|
| 4,862,888 | A | 9/1989 | Yessik |
| 5,281,241 | A | 1/1994 | Patel |
| 5,323,766 | A | 6/1994 | Uram |
| 5,738,677 | A | 4/1998 | Colvard et al. |
| 5,755,716 | A | 5/1998 | Garito et al. |
| 5,865,831 | A | 2/1999 | Cozean et al. |
| 6,197,056 | B1 | 3/2001 | Schachar |
| 6,283,974 | B1 | 9/2001 | Alexander |
| 6,743,221 | B1 | 6/2004 | Hobart et al. |
| 7,443,296 | B2 | 10/2008 | Mezhinsky et al. |
| 7,568,619 | B2 | 8/2009 | Todd et al. |
| 7,801,271 | B2 | 9/2010 | Gertner et al. |
| 9,489,785 | B2 | 11/2016 | Klammer et al. |
| 9,642,746 | B2 | 5/2017 | Berlin |
| 10,383,689 | B2 | 8/2019 | Berlin |
| 11,076,933 | B2 | 8/2021 | Junger et al. |
| 11,076,992 | B2 | 8/2021 | Junger et al. |
| 11,103,382 | B2 | 8/2021 | Junger et al. |
| 11,234,866 | B2 | 2/2022 | Junger et al. |
| 11,389,239 | B2 | 7/2022 | Junger et al. |
| 11,464,677 | B2 | 10/2022 | Junger et al. |
| 11,529,260 | B2 | 12/2022 | Junger et al. |
| 2002/0013572 | A1 | 1/2002 | Berlin |
| 2002/0183726 | A1 | 12/2002 | Elbrecht et al. |
| 2004/0082939 | A1 | 4/2004 | Berlin |
| 2004/0114879 | A1 | 6/2004 | Hiereth et al. |
| 2004/0147985 | A1 | 7/2004 | MacFarland et al. |
| 2005/0192480 | A1 | 9/2005 | Toriya et al. |
| 2005/0283148 | A1 | 12/2005 | Janssen et al. |
| 2006/0111699 | A1 | 5/2006 | Neuberger |
| 2006/0244652 | A1 | 11/2006 | Tethrake et al. |
| 2007/0027443 | A1 | 2/2007 | Rose et al. |
| 2007/0122096 | A1 | 5/2007 | Temelkuran et al. |
| 2007/0147752 | A1 | 6/2007 | Weisberg et al. |
| 2007/0219601 | A1 | 9/2007 | Neuberger |
| 2007/0265602 | A1 | 11/2007 | Mordaunt et al. |
| 2008/0054073 | A1 | 3/2008 | Charles |
| 2008/0082078 | A1 | 4/2008 | Berlin |
| 2008/0097415 | A1 | 4/2008 | Zimare et al. |
| 2008/0108981 | A1 | 5/2008 | Telfair et al. |
| 2008/0108983 | A1 | 5/2008 | Nadolski |
| 2008/0161781 | A1 | 7/2008 | McArdle et al. |
| 2008/0269734 | A1 | 10/2008 | Vila Echague et al. |
| 2009/0030300 | A1 | 1/2009 | Hhaboussi et al. |
| 2009/0118715 | A1 | 5/2009 | Mansour |
| 2009/0157064 | A1 | 6/2009 | Hodel |
| 2010/0019125 | A1 | 1/2010 | Stefani et al. |
| 2010/0068141 | A1 | 3/2010 | Kaushal et al. |
| 2010/0324543 | A1 | 12/2010 | Kurtz et al. |
| 2011/0295243 | A1 | 12/2011 | Peyman |
| 2011/0301507 | A1 | 12/2011 | Romano et al. |
| 2012/0275481 | A1 | 11/2012 | Riggs |
| 2013/0041357 | A1 | 2/2013 | Neuberger |
| 2013/0085484 | A1 | 4/2013 | Van Valen et al. |
| 2014/0058367 | A1 | 2/2014 | Dantus |
| 2014/0121653 | A1* | 5/2014 | Abe .............. A61F 9/008 606/4 |
| 2014/0188096 | A1 | 7/2014 | Chia et al. |
| 2014/0316388 | A1 | 10/2014 | Hipsley |
| 2015/0051607 | A1 | 2/2015 | Hajishah et al. |
| 2015/0080783 | A1 | 3/2015 | Berlin |
| 2015/0148615 | A1 | 5/2015 | Brennan et al. |
| 2015/0217133 | A1 | 8/2015 | Angeley et al. |
| 2015/0297408 | A1 | 10/2015 | Dolzan et al. |
| 2015/0305811 | A1 | 10/2015 | Neuberger |
| 2015/0366706 | A1 | 12/2015 | Belkin et al. |
| 2015/0374549 | A1 | 12/2015 | Scott |
| 2017/0100041 | A1 | 4/2017 | Kasamatsu et al. |
| 2017/0202708 | A1 | 7/2017 | Berlin |
| 2017/0304001 | A1 | 10/2017 | Searle et al. |
| 2018/0000337 | A1 | 1/2018 | Chen et al. |
| 2018/0042772 | A1 | 2/2018 | Mansour |
| 2018/0263647 | A1 | 9/2018 | Aljuri et al. |
| 2018/0303667 | A1 | 10/2018 | Peyman |
| 2018/0353328 | A1 | 12/2018 | Bacher et al. |
| 2018/0360310 | A1 | 12/2018 | Berlin |
| 2019/0105200 | A1 | 4/2019 | Hipsley |
| 2019/0117459 | A1 | 4/2019 | Berlin |
| 2019/0262071 | A1 | 8/2019 | Thorn et al. |
| 2020/0078216 | A1 | 3/2020 | Raksi |
| 2020/0078217 | A1 | 3/2020 | Raksi |
| 2020/0330157 | A1 | 10/2020 | Junger et al. |
| 2020/0330181 | A1 | 10/2020 | Junger et al. |
| 2020/0330266 | A1 | 10/2020 | Junger et al. |
| 2020/0330274 | A1 | 10/2020 | Junger et al. |
| 2020/0330275 | A1 | 10/2020 | Junger et al. |
| 2020/0330279 | A1 | 10/2020 | Junger et al. |
| 2020/0330280 | A1 | 10/2020 | Junger et al. |
| 2020/0330281 | A1 | 10/2020 | Junger et al. |
| 2020/0390600 | A1 | 12/2020 | Perera et al. |
| 2021/0235986 | A1 | 8/2021 | Juhasz et al. |
| 2021/0259880 | A1 | 8/2021 | Newton et al. |
| 2021/0298945 | A1 | 9/2021 | Juhasz et al. |
| 2022/0022997 | A1 | 1/2022 | Junger et al. |
| 2022/0023098 | A1 | 1/2022 | Junger et al. |
| 2022/0031513 | A1 | 2/2022 | Junger et al. |
| 2022/0151828 | A1 | 5/2022 | Junger et al. |
| 2022/0183882 | A1 | 6/2022 | Mosaed et al. |
| 2022/0183887 | A1 | 6/2022 | Junger et al. |
| 2022/0280343 | A1 | 9/2022 | Junger et al. |
| 2022/0387107 | A1 | 12/2022 | Junger et al. |
| 2022/0387218 | A1 | 12/2022 | Junger et al. |

FOREIGN PATENT DOCUMENTS

| | | |
|---|---|---|
| DE | 10138984 A1 | 3/2003 |
| EP | 1835862 B1 | 6/2011 |
| EP | 2120760 B1 | 9/2015 |
| WO | 2019060756 A1 | 3/2019 |
| WO | WO 2020215062 A1 | 10/2020 |
| WO | WO 2020215064 A1 | 10/2020 |
| WO | WO 2020215066 A1 | 10/2020 |
| WO | WO 2020215067 A1 | 10/2020 |
| WO | WO 2020215068 A1 | 10/2020 |
| WO | WO 2020215069 A1 | 10/2020 |
| WO | WO 2020215071 A1 | 10/2020 |
| WO | WO 20200215073 A1 | 10/2020 |

OTHER PUBLICATIONS

Francis et al., "Combined Cataract Extraction and Trabeculotomy by the Internal Approach for Coexisting Cataract and Open-Angle Glaucoma: Initial Results", Journal of Cataract & Refractive Surgery, Jul. 1, 2008, vol. 34, pp. 1096-1103.

Wilmsmeyer et al., "Excimer Laser Trabeculotomy: A New, Minimally Invasive Procedure for Patients With Glaucoma", Graefe's Archive for Clinical and Experimental Ophthalmology, Oct. 19, 2005, vol. 244, pp. 670-676.

Crandall, Alan, "Combining Cataract and Glaucoma Surgery", Review of Ophthalmology, 1-4, Jun. 13, 2008.

ExTra Operating Instructions, Manufacturer: MLase AG, published prior to Jan. 1, 2018. Third Party Submission in 010402.

Grover, Davinder S. "When You Have Cataracts and Glaucoma", Glaucoma Research Foundation, Oct 29, 2017.

Investigation Testing Authorization Application, YUI Laser AG Published Jan. 1, 2016. Third Party Submission in 010302.

(56) References Cited

OTHER PUBLICATIONS

Leung et al., "Anterior Chamber Angle Measurement with Anterior Segment Optical Coherence Tomography: A Comparison between Slit Lamp OCT and Visante OCT", Investigative Ophthalmology & Visual Science, vol. 49, No. 8, pp. 3469-3474, Aug. 2008.

Taliaferro, Kevin et al. "Excimer Laser Trabeculostomy Normalizing IOP and Restoring Physiologic Outflow in Glaucoma." Glaucoma Today, 2009, pp. 45-47 (Year: 2009).

Toteberg-Harms, et al., "Cataract surgery combined with excimer laser trabeculotomy to lower intraocular pressure: effectiveness dependent on preoperative IOP." BMC ophthalmology, vol. 13, No. 1, pg. 24 (2013).

Tsai, James C. "High Eye Pressure and Glaucoma", Glaucoma Research Foundation, Oct. 29, 2017.

Berlin, et al., "Excimer Laser Trabeculostomy: An Effective Microinvasive Glaucoma Surgery Procedure for Open-Angle Glaucoma", published Dec. 19, 2013 Third Party Submission in 010503.

\* cited by examiner

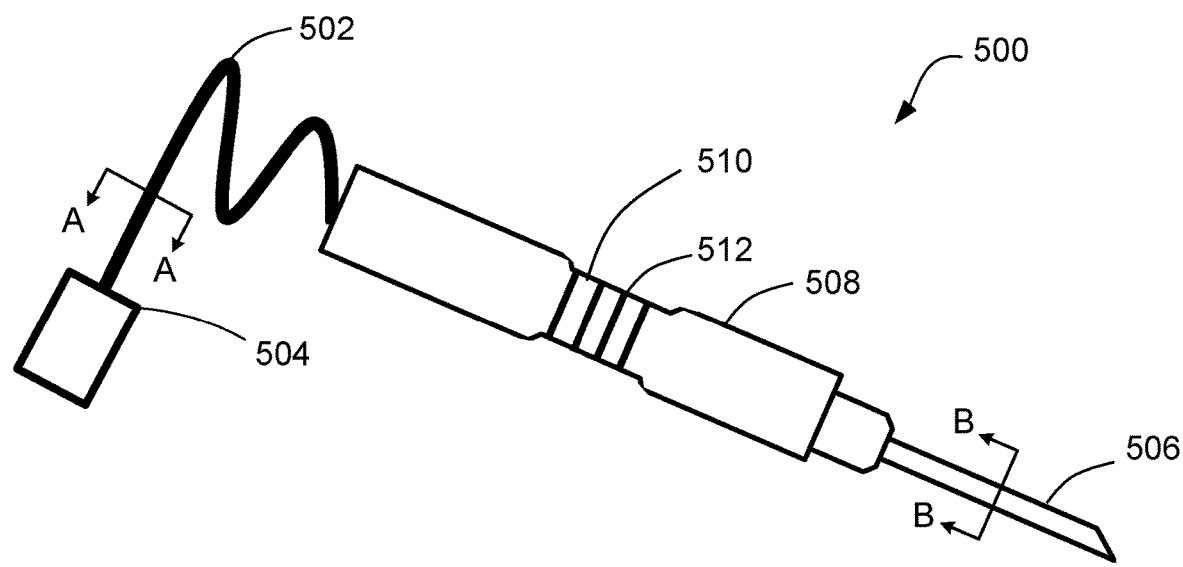
FIG. 5
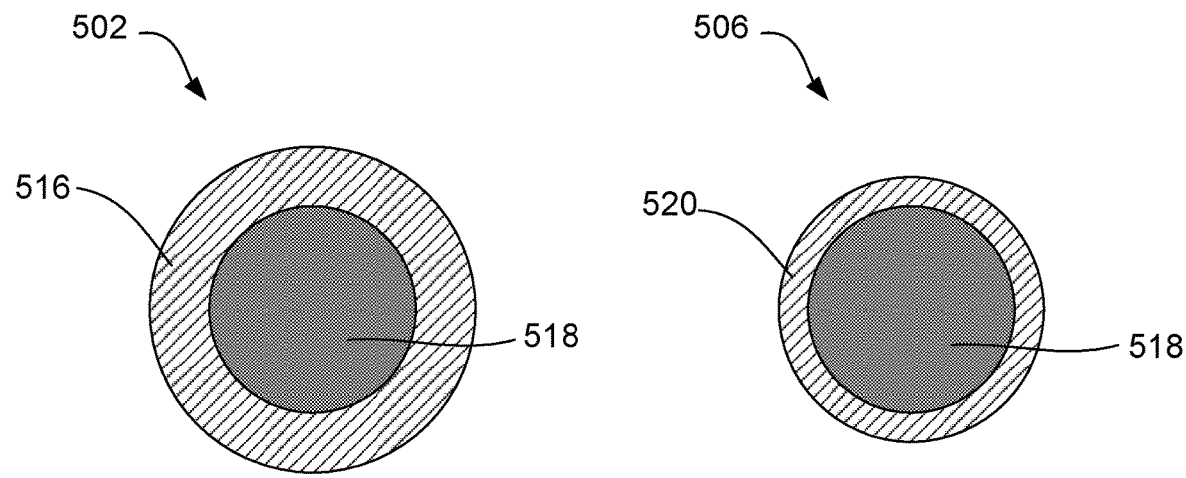
FIG. 6  FIG. 7

SYSTEMS AND METHODS FOR PERFORMING AN INTRAOCULAR PROCEDURE FOR TREATING AN EYE CONDITION

RELATED APPLICATIONS

This application is a continuation patent application of U.S. application Ser. No. 17/400,191, filed Aug. 12, 2021, which is a continuation patent application of U.S. application Ser. No. 16/389,359, filed Apr. 19, 2019, now U.S. Pat. No. 11,103,382, all of which are incorporated herein by reference in their entireties.

TECHNICAL FIELD

The disclosure relates to medical devices, and, more particularly, to an excimer laser system including a means for calibrating laser output to compensate for increased variation in laser optical fibers.

BACKGROUND

In the medical industry, there are many surgical devices, instruments, and systems comprised of individual components that must work together properly to ensure treatment is performed safely and effectively. It is critical that any given component falls within an acceptable tolerance to ensure that the component physically fits and interacts appropriately with other components and functions as intended.

The actual production of any product (or operation of any system) involves some inherent variation of input and output. Measurement error and statistical uncertainty are also present in all measurements. Accordingly, tolerance is an inherent aspect when designing a device, instrument, or system. The concept of tolerance, sometimes referred to as engineering tolerance, relates to the permissible limit or limits of variation in a physical dimension of the component, a measured value or physical property of the component, spacing between the component and another component, and the like. Accordingly, if a component falls outside of a permissible tolerance (i.e., the component is too small, too large, fails to have acceptable properties, etc.), then the overall device, instrument, or system will fail to perform as designed.

One example of a surgical system composed of multiple components is a medical laser system. The medical laser system generally consists of a laser unit and a separate laser probe having an optical fiber for directing laser radiation from the laser unit to a treatment area. Laser units provide laser light at specific wavelengths and, as a result, may be designed to perform specific procedures. For example, certain procedures may require photocoagulation of a target tissue, which occurs upon delivery of laser radiation at a first wavelength, while other procedures may require photoablation of a target tissue, which occurs upon delivery of laser radiation at a second wavelength. In turn, optical fibers to be used with these laser systems may have specific dimensions, material compositions, and/or functional properties (i.e., operation at specific temperatures and wavelengths) so as to function as intended with the corresponding laser unit.

While current laser units allow for some tolerance (i.e., optical fiber dimensions, properties, or conditions may have some variation without significantly affecting functioning of the laser system), the range of permissible tolerance is exceedingly tight. For example, optical fibers have a very small diameter which is generally measured on the micron scale. The diameter of the optical fiber may impact the transmission of laser radiation through the optical fiber and thus may impact the laser radiation emitted from the delivery tip of the optical fiber. As such, there is very little room for variation in the manufacture of optical fibers. Manufacturing costs are increases as a result of the high degree of precision required to make sure the diameter of an optical fiber falls within the permissible tolerance. Furthermore, if a given optical fiber falls outside of a permissible tolerance (i.e., the diameter is too be or too small), use of the noncompliant optical fiber may result in transmission of laser radiation that is not at the desired wavelength. In turn, use of a noncompliant optical fiber runs the risk of providing an ineffective treatment and, in some instance, can cause additional unintended damage and harm.

SUMMARY

The present invention provides a system for calibrating output from a laser source to compensate for increased variation in laser optical fibers. In such a system, the elements generally include a laser source for generating laser energy to be provided to one of a plurality of laser probes couplable thereto. Each laser probe includes an optical fiber, including a fiber optic core, adapted to direct laser radiation from the laser source, through the fiber, and to a desired the treatment area. The system further includes a laser management system for managing the laser source. The management system includes a control system configured to adjust laser energy output from the laser source to any given laser probe to maintain a consistent level of laser radiation delivered to the target area, despite variation in the fiber optic core of any given laser probe.

More specifically, as part of the initial setup, the control system receives data associated with a laser probe coupled to the laser source. The data may include one or more dimensions of the fiber optic core of the laser probe, including fiber optic core diameter. The data is then analyzed by the controller and, based on the analysis, a determination of an optimum level of laser energy output from the laser source is made. The optimum level of laser energy output from the laser source is based on a correlation of the laser probe data, such as specific dimensions of the fiber optic core, with calibration data. The calibration data may generally include a plurality of sets of values, wherein each set of values may include a laser energy output level from the laser source, a diameter of a fiber optic core of a laser probe to receive the laser energy output level, and the resulting wavelength value of laser radiation emitted from the delivery tip of the laser probe. In a preferred embodiment, the resulting wavelength value of laser radiation to be emitted from the delivery tip remains constant, regardless of the diameter of the fiber optic core. In such an embodiment, the laser management system (i.e., the control system) automatically adjusts the laser energy output level from the laser source (i.e., increases or decreases output level) for any given diameter of a fiber optic core so as to maintain the emission of laser radiation upon a target area at a consistent wavelength, despite variation in the diameter of fiber optic cores from the plurality of laser probes.

Accordingly, the system of the present invention is able to compensate for wide range of variations across a plurality of laser probes by simply adjusting output of the laser source to account for such variations. In turn, the manufacture tolerance for optical fibers improves as less precision is required during the manufacturing process, which reduces overall costs. Furthermore, by fine tuning of the laser output, the laser radiation is maintained at a consistent wavelength, ensuring that the target area is treated as intended and patient safety is maintained.

BRIEF DESCRIPTION OF THE DRAWINGS

FIG. 5 shows an embodiment of a probe for use with the excimer laser system.

FIG. 6 shows a cross-sectional view of the probe taken along line A-A of FIG. 5.

FIG. 7 shows a cross-sectional view of the probe taken along line B-B of FIG. 5.

DETAILED DESCRIPTION

The invention provides a system for calibrating output from a laser source to compensate for increased variation in laser optical fibers. In such a system, the elements generally include a laser source for generating laser energy to be provided to one of a plurality of laser probes couplable thereto. Each laser probe includes an optical fiber, including a fiber optic core, adapted to direct laser radiation from the laser source, through the fiber, and to a desired the treatment area. The system further includes a laser management system for managing the laser source. The management system includes a control system configured to adjust laser energy output from the laser source to any given laser probe to maintain a consistent level of laser radiation delivered to the target area, despite variation in the fiber optic core of any given laser probe.

Accordingly, the system of the present invention is able to compensate for wide range of variations across a plurality of laser probes by simply adjusting output of the laser source to account for such variations. In turn, the manufacture tolerance for optical fibers improves as less precision is required during the manufacturing process, which reduces overall costs. Furthermore, by fine tuning of the laser output, the laser radiation is maintained at a consistent wavelength, ensuring that the target area is treated as intended and patient safety is maintained.

The system of the present invention is particularly well suited for intraocular procedures in which laser treatment of target tissues is desired. In particular, the laser source, laser management system, and laser probes of the present invention are preferably used for treating glaucoma and useful in performing a laser trabeculostomy. However, it should be noted that the system consistent with the present disclosure can be used in any laser treatment of various conditions, including other eye conditions (i.e., diabetic eye diseases, such as proliferative diabetic retinopathy or macular oedema, cases of age-related macular degeneration, retinal tears, and retinopathy of prematurity, and laser-assisted in situ keratomileusis (LASIK) to correct refractive errors, such as short-sightedness (myopia) or astigmatism) as well as other conditions in general and other practice areas (non-ocular practice areas).

Figure 1:
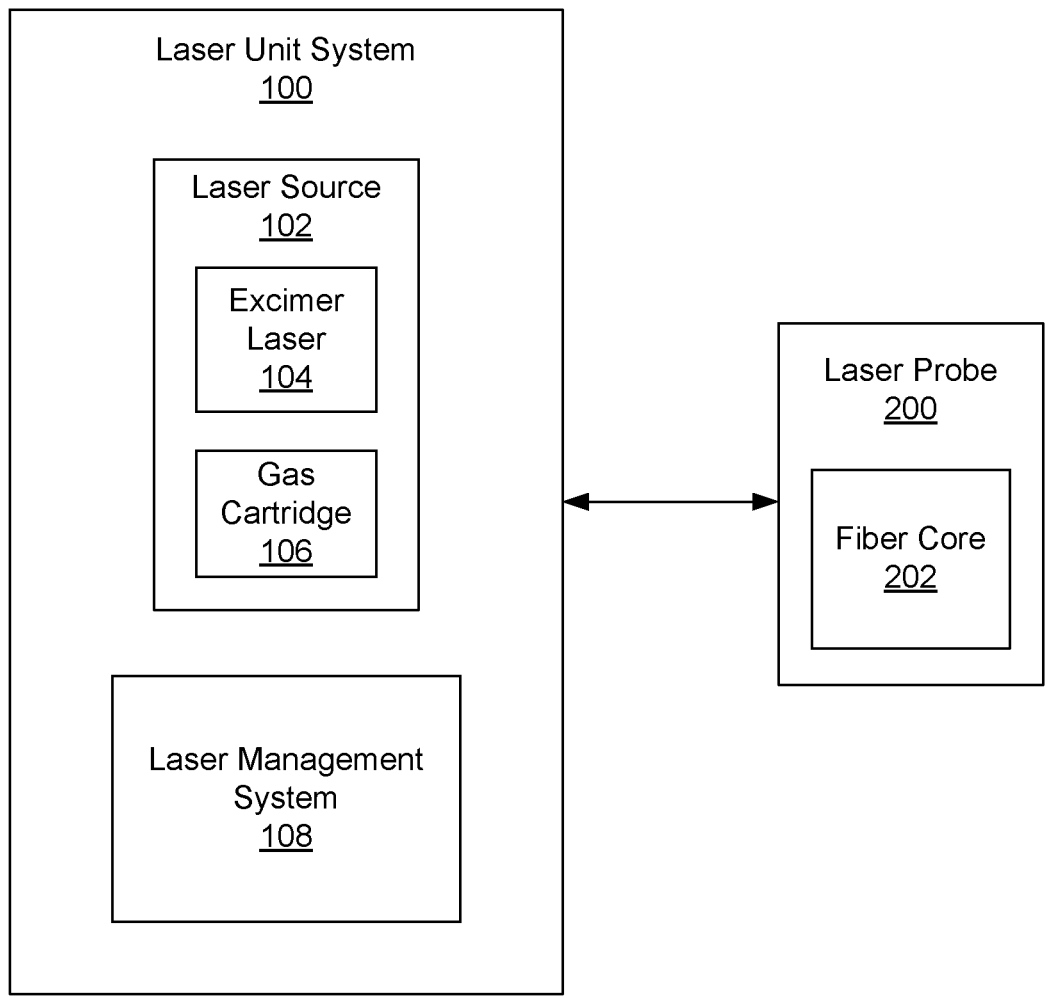
FIG. 1 diagrams an excimer laser system of the present disclosure.

FIG. 1 diagrams an excimer laser system, including a laser unit system 100 and a laser probe 200 to be attached to the laser unit system 100. The system 100 includes a laser source 102, and a laser management system 108. The laser probe 200 includes a fiber core 204. As will be described in greater detail herein, many of the components of the laser unit system 100 may be contained in a housing, such as a moveable platform, to be provided in a setting in which the procedure is to be performed (e.g., operating room, procedure room, outpatient office setting, etc.) and the probe 200 may connect to the housing for use during treatment. Upon coupling the probe 200 to the housing, the fiber core 202 is coupled to the laser source 102 and adapted to direct laser radiation from the laser source 102, through the fiber, and to the treatment area.

The laser source 102 includes an excimer laser 104 and a gas cartridge 108 for providing the appropriate gas combination to the laser 104. The excimer laser 104 is a form of ultraviolet laser that generally operates in the UV spectral region and generates nanosecond pulses. The excimer gain medium (i.e., the medium contained within the gas cartridge 106) is generally a gas mixture containing a noble gas (e.g., argon, krypton, or xenon) and a reactive gas (e.g., fluorine or chlorine). Under the appropriate conditions of electrical stimulation and high pressure, a pseudo-molecule called an excimer (or in the case of noble gas halides, exciplex) is created, which can only exist in an energized state and can give rise to laser light in the UV range.

Laser action in an excimer molecule occurs because it has a bound (associative) excited state, but a repulsive (dissociative) ground state. Noble gases such as xenon and krypton are highly inert and do not usually form chemical compounds. However, when in an excited state (induced by electrical discharge or high-energy electron beams), they can form temporarily bound molecules with themselves (excimer) or with halogens (exciplex) such as fluorine and chlorine. The excited compound can release its excess energy by undergoing spontaneous or stimulated emission, resulting in a strongly repulsive ground state molecule which very quickly (on the order of a picosecond) dissociates back into two unbound atoms. This forms a population inversion. The excimer laser 104 of the present system 100 is an XeCl excimer laser and emits a wavelength of 308 nm.

Figure 2:
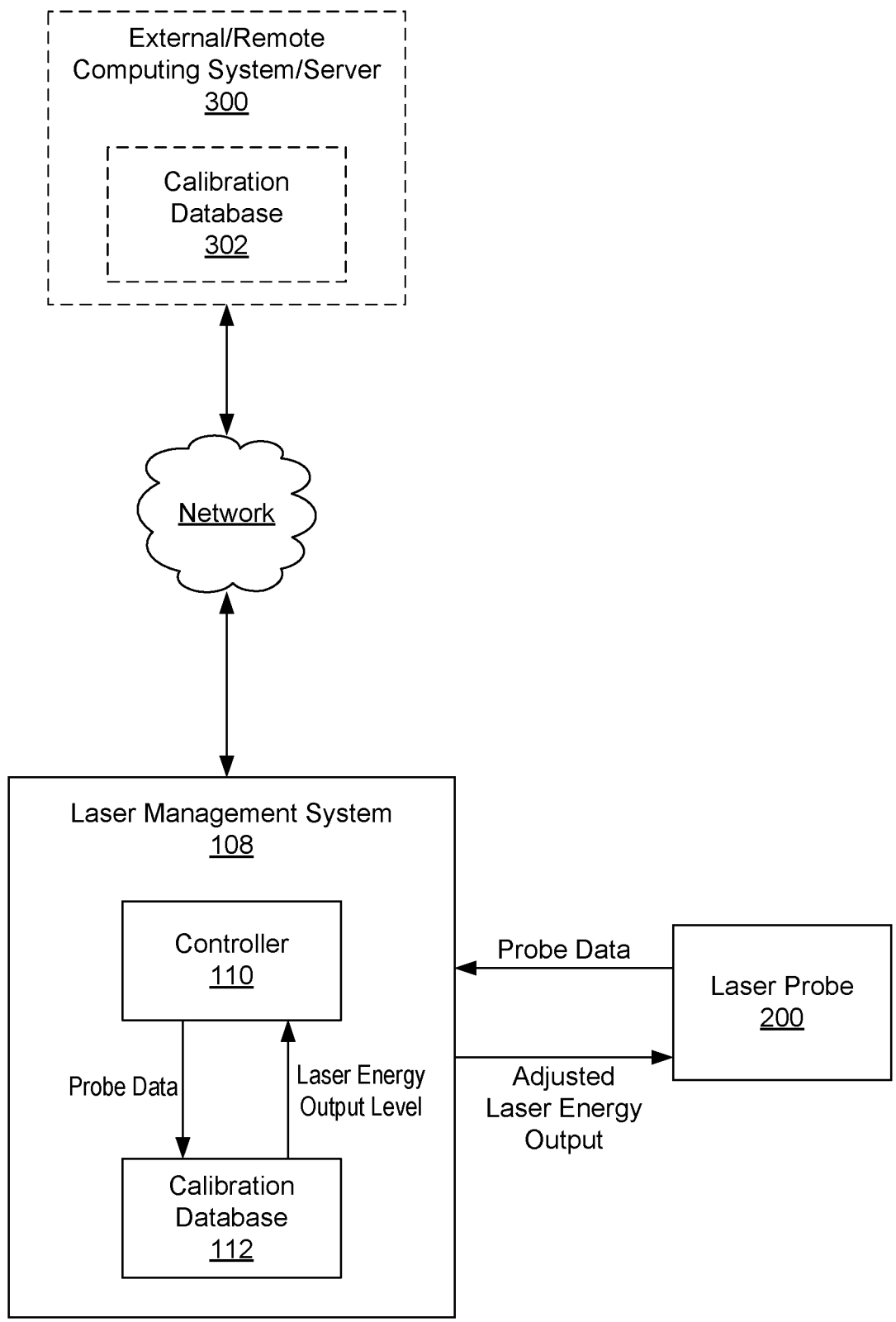
FIG. 2 diagrams the excimer laser system of the present disclosure and a means for calibrating laser output to compensate for increased variation in optical fibers of laser probes.

The laser management system 108 manages the laser source 102. In particular, as shown in FIG. 2, the laser management system 108 includes a controller 110 (also referred to herein as a "control system 110"). The controller 110 provides an operator (i.e., surgeon or other medical professional) with control over the output of laser signals (from the laser source 102 to the fiber core 202) and, in turn, control over the transmission of laser energy from the fiber core 202 of the probe 200. However, prior to providing an operator with control over laser output, the laser management system 108 provides a calibration process in which laser energy output from the laser source 102 to the laser probe 200 is calibrated to maintain a consistent level of laser radiation delivered from the probe 200 to the target area, despite any variation in the fiber optic core 202 of the probe 200.

Figure 3:
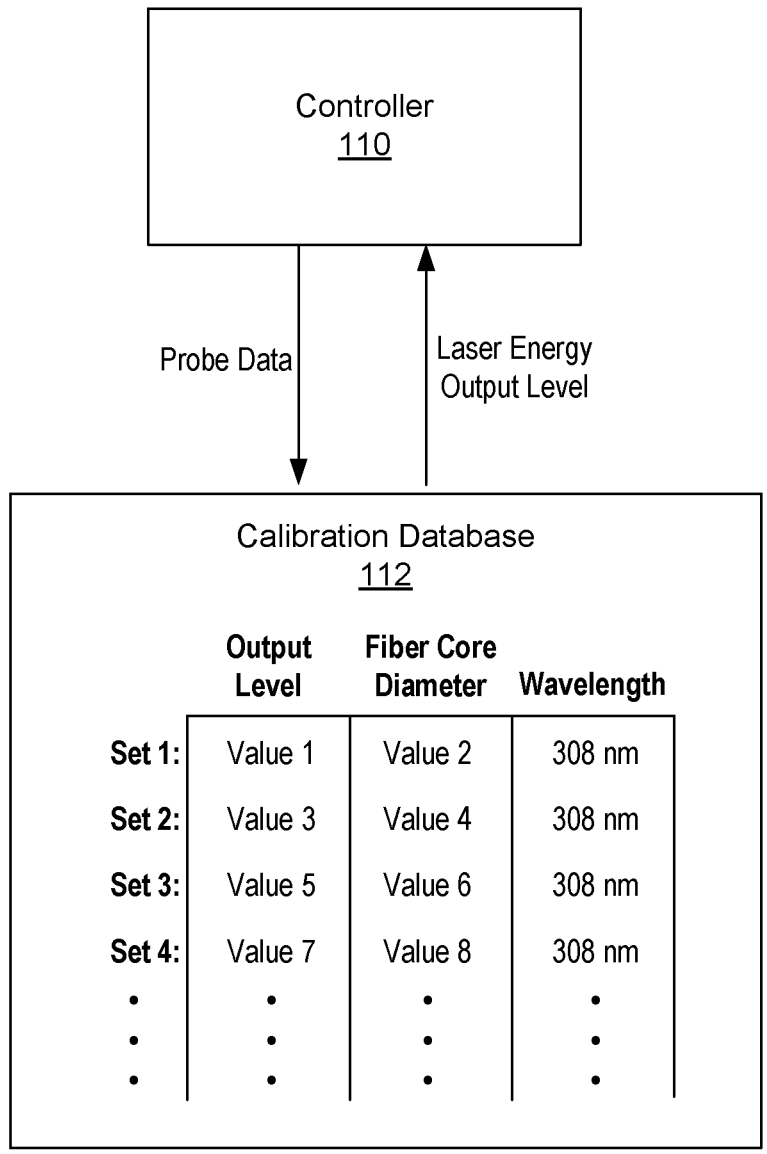
FIG. 3 diagrams a process of calibrating laser output, including adjustment of laser energy output from the laser source to a laser probe to account for variation in the fiber optic core of the laser probe.

FIG. 2 diagrams the laser unit system 100 and calibration of laser output to a laser probe 200 to be used with the system 100 to account for variation in the fiber optic core of the laser probe 200. FIG. 3 diagrams a process of calibrating laser output, including adjustment of laser energy output from the laser source to a laser probe to account for variation in the fiber optic core 202 of the laser probe 200.

As part of the initial setup, the controller 110 receives data associated with a laser probe coupled to the laser source 102. In this instance, data from laser probe 200 is provided to the controller 110. This data may be manually entered (via a user interface provided on the system 100) or may be automatically read from readable device or label on the probe 200 via an associated reader of the system 100. The data may include physical characteristics of the probe 200, including, but not limited to, physical dimensions of the fiber optic core 202, one or more measured values or physical properties of the fiber optic core 202, and physical dimensions and/or measured values or physical properties of other components of the probe 200. In one embodiment, the data includes a diameter of the fiber optic core 202.

The data is then analyzed by the controller 110 and, based on the analysis, a determination of an optimum level of laser energy output from the laser source 102 is made. The analysis is based on a correlation of the laser probe data, such as specific dimensions of the fiber optic core, with calibration data. The calibration data is stored in a database, either a local database (i.e., calibration database 112) forming part of the laser unit system 100, or a remote database hosted via a remote server 300 (i.e., calibration database 302). For example, in some embodiments, the system 100 may communicate and exchange data with a remote server 300 over a network. The network may represent, for example, a private or non-private local area network (LAN), personal area network (PAN), storage area network (SAN), backbone network, global area network (GAN), wide area network (WAN), or collection of any such computer networks such as an intranet, extranet or the Internet (i.e., a global system of interconnected network upon which various applications or service run including, for example, the World Wide Web).

The calibration data may generally include a plurality of sets of values, wherein each set of values may include a laser energy output level from the laser source, a diameter of a fiber optic core of a laser probe to receive the laser energy output level, and the resulting wavelength value of laser radiation emitted from the delivery tip of the laser probe. In a preferred embodiment, the resulting wavelength value of laser radiation to be emitted from the delivery tip remains constant, regardless of the diameter of the fiber optic core. In such an embodiment, the laser management system (i.e., the control system) automatically adjusts the laser energy output level from the laser source (i.e., increases or decreases output level) for any given diameter of a fiber optic core so as to maintain the emission of laser radiation upon a target area at a consistent wavelength, despite variation in the diameter of fiber optic cores from the plurality of laser probes.

The controller 110 may include software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices. "Circuitry", as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry. For example, the controller 104 may include a hardware processor coupled to non-transitory, computer-readable memory containing instructions executable by the processor to cause the controller to carry out various functions of the laser system 100 as described herein, including the calibration process. For example, the controller 110 may include custom, proprietary, known and/or after-developed statistical analysis code (or instruction sets), hardware, and/or firmware that are generally well-defined and operable to receive two or more sets of data and identify, at least to a certain extent, a level of correlation and thereby associate the sets of data with one another based on the level of correlation.

Figure 4:
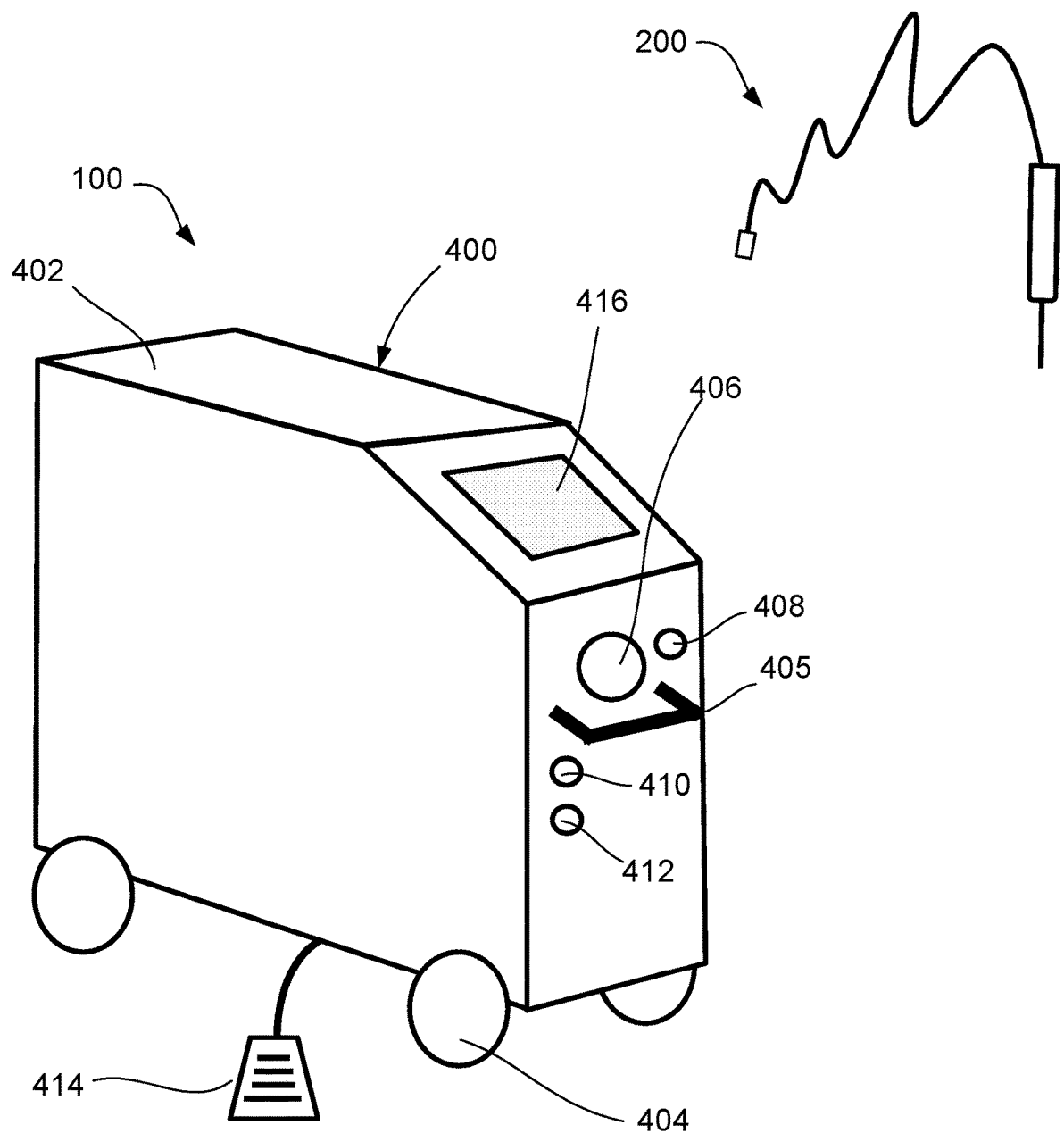
FIG. 4 shows an embodiment an excimer laser unit.

FIG. 4 shows an embodiment an excimer laser unit 100 provided in an instrument 400. As previously described, one or more components of the system 100 can be contained within the instrument 400. In the present embodiment, the laser source 102 (including the excimer laser 104 and gas cartridge 106) and laser management system 108, including the controller 110, are contained within a housing 402. The housing 402 has wheels 404 and is portable. The instrument 400 further includes a push-pull handle 405 which assists with portability of the instrument 400. The instrument 400 further includes a connection port 406 for receiving a connecting end of the laser probe 200 to establish a connection between the fiber core 202 and the laser source 102. The instrument 400 further includes various inputs for the operator, such as a fiber probe cap holder 408, an emergency stop button 410, and a power switch 412. The instrument 400 further includes a foot pedal 414 extending from the housing 402 and is operable to provide control over the delivery of shots from the excimer laser 104 to the fiber core 202 of the probe 200. The instrument 400 further includes a display 416, which may be in the form of an interactive user interface. In some examples, the interactive user interface displays patient information, machine settings, and procedure information. As previously described, an operator may manually input the laser probe data via the interactive user interface to thereby provide such data to the laser management system 108 and controller 110. However, in some embodiments, the data may be automatically read from a readable device or label on the probe 200 via an associated reader of the system 100.

FIG. 5 shows an embodiment of a probe 500 for use with the excimer laser system 100. The probe 500 is a single use, disposable unit. The probe 500 generally includes a fiber core coupled to the laser source 102 by way of a connector 502 (elongated cord) extending from the body of the probe 500 and having a connection assembly 504 configured to be received within the connection port 406 of the instrument 400. The probe 500 further includes a delivery tip 506 from which laser energy (from the fiber core) may be emitted. The probe 500 includes a handheld body 508, which may include a finger grip 510 with ridges or depressions 512. The body 508 of the handheld probe 500 may be metal or plastic.

FIGS. 6 and 7 show cross-sectional views of the probe 500 taken along line A-A and line B-B of FIG. 5, respectively. As shown, a fiber optic core 518 runs through the probe 500 and forms part of the connector 502. A protective sheath 516 surrounds the fiber optic core 518. In some examples, the protective sheath 516 is a protective plastic or rubber sheath. The fiber optic core 518 further form part of the delivery tip 506 of the probe 500. A metal jacket 520 surrounds the fiber optic core 518 and optical fiber 520. In some instances, a stainless steel jacket 520 surrounds and protects the fiber optic core 518.

Figure 8:
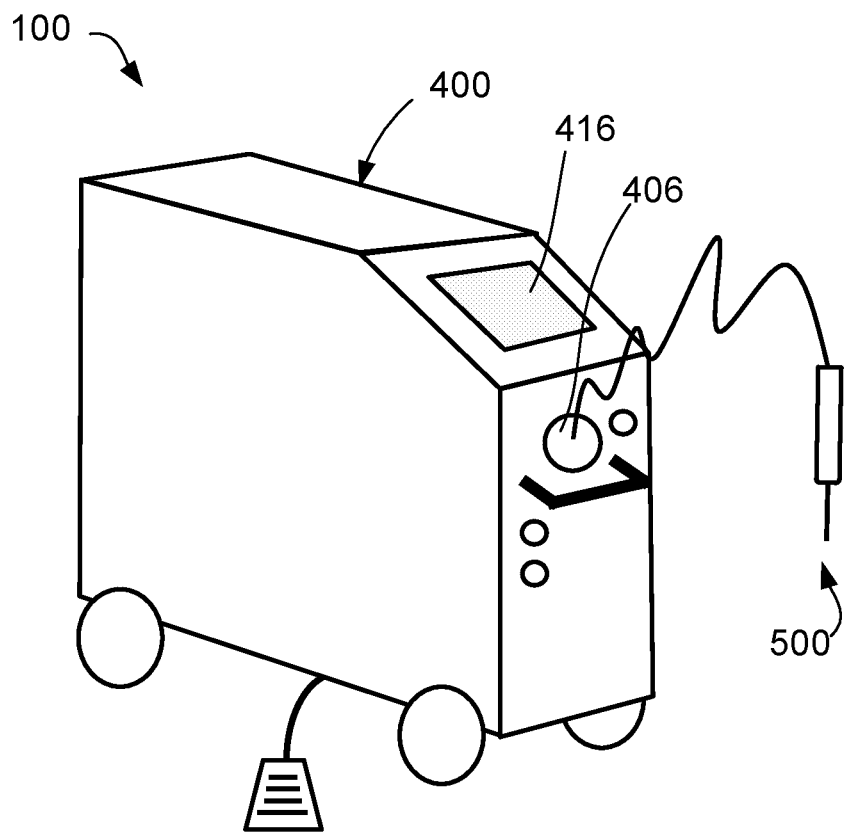
FIG. 8 shows an embodiment a laser probe attached to an excimer laser unit.
Figure 9:
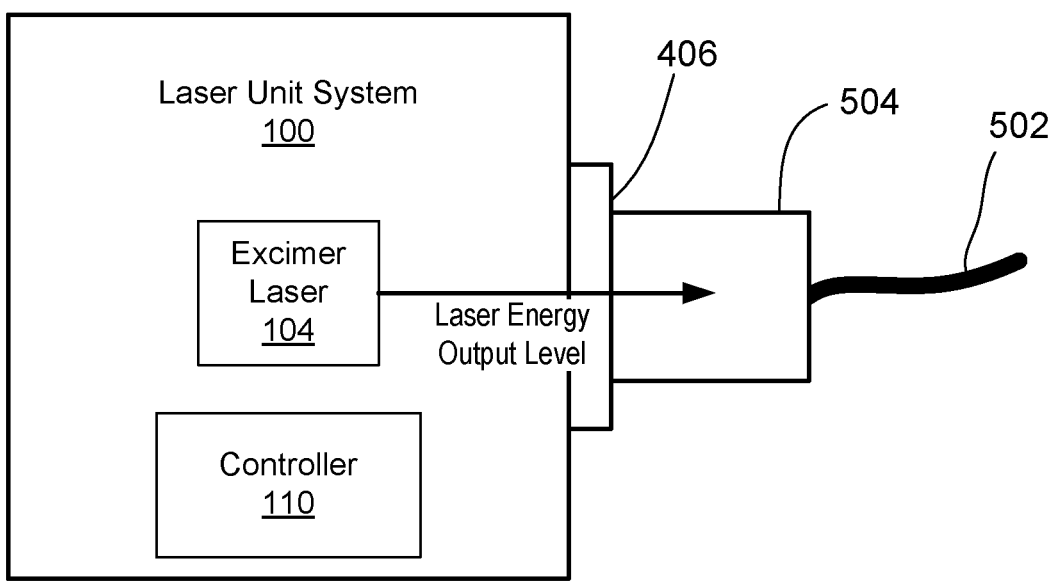
FIG. 9 shows an enlarged view of a connection between the laser probe and the excimer unit and delivery of an adjusted laser energy output level to the laser probe based on calibration techniques.

FIG. 8 shows an embodiment a laser probe 500 attached to a laser unit system 100. As previously described, upon attachment of the laser probe 500 to the system 100 (i.e., coupling between the connection assembly 504 of the probe 500 and connection port 406 of the system 400), the laser management system 108 (including the controller 110) perform calibration processes prior to use of the probe 500. In particular, data associated with characteristics of the probe 500, such as the diameter of the fiber optic core, is provided to the laser management system 108. The data is then analyzed by the controller 110 and, based on the analysis, a determination of an optimum level of laser energy output from the laser source is made. FIG. 9 shows an enlarged view of a connection between the laser probe 500 and the system 100 and delivery of an adjusted laser energy output level to the laser probe based on calibration techniques. The optimum level of laser energy output from the laser source is based on a correlation of the laser probe data, such as specific dimensions of the fiber optic core, with calibration data. The controller 110 automatically adjusts the laser energy output level from the laser source (i.e., increases or decreases output level) for any given diameter of a fiber optic core so as to maintain the emission of laser radiation upon a target area at a consistent wavelength, despite variation in the diameter of fiber optic cores from the plurality of laser probes.

Accordingly, the system of the present invention is able to compensate for wide range of variations across a plurality of laser probes by simply adjusting output of the laser source to account for such variations. In turn, the manufacture tolerance for optical fibers improves as less precision is required during the manufacturing process, which reduces overall costs. Furthermore, by fine tuning of the laser output, the laser radiation is maintained at a consistent wavelength, ensuring that the target area is treated as intended and patient safety is maintained.

As used in any embodiment herein, the term "module" may refer to software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices. "Circuitry", as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry. The modules may, collectively or individually, be embodied as circuitry that forms part of a larger system, for example, an integrated circuit (IC), system on-chip (SoC), desktop computers, laptop computers, tablet computers, servers, smart phones, etc.

Any of the operations described herein may be implemented in a system that includes one or more storage mediums having stored thereon, individually or in combination, instructions that when executed by one or more processors perform the methods. Here, the processor may include, for example, a server CPU, a mobile device CPU, and/or other programmable circuitry.

Also, it is intended that operations described herein may be distributed across a plurality of physical devices, such as processing structures at more than one different physical location. The storage medium may include any type of tangible medium, for example, any type of disk including hard disks, floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, Solid State Disks (SSDs), magnetic or optical cards, or any type of media suitable for storing electronic instructions. Other embodiments may be implemented as software modules executed by a programmable control device. The storage medium may be non-transitory.

As described herein, various embodiments may be implemented using hardware elements, software elements, or any combination thereof. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for performing intraocular procedures for treating eye conditions, said method comprising:
   connecting a first probe of a plurality of excimer laser probes to an excimer laser source, wherein:
   the excimer laser source is configured to generate laser energy to be provided to each of the plurality of excimer laser probes, and the plurality of excimer laser probes are single use and disposable, such that the plurality of excimer laser probes are each coupleable, one at a time, to said excimer laser source;
   receiving, by a processor in communication with the excimer laser source after the first probe is connected to the excimer laser source, first data from a first readable device or first label of the first probe read automatically by a reader in communication with the processor, wherein the data is indicative of at least a first diameter of a first fiber optic core of the first probe;
   determining, by the processor, a first laser energy output level to transmit to the first probe;
   receiving, by the processor, a first signal indicative of a user control of the excimer laser source;
   transmitting, by the processor in response to receiving the first signal, a second signal indicative of the first laser energy output level to the excimer laser source, wherein the second signal is configured to cause the first probe to emit first energy from the excimer laser source at the first laser energy output level;
   disconnecting the first probe from the excimer laser source;
   connecting a second probe of the plurality of excimer laser probes to the excimer laser source after the first probe is disconnected;
   receiving, by the processor after the second probe is connected to the excimer laser source, second data from a second readable device or second label of the second probe read automatically by the reader, wherein second data is indicative of at least a second diameter of a second fiber optic core of the second probe;
   determining, by the processor, a second laser energy output level to transmit to the second probe; receiving, by the processor, a third signal indicative of the user control of the excimer laser source; and
   transmitting, by the processor in response to receiving the third signal, a fourth signal indicative of the second laser energy output level to the excimer laser source, wherein the fourth signal is configured to cause the second probe to emit second energy from the excimer laser source at the second laser enemy output level.

2. The method of claim 1, further comprising correlating, by the processor, the first data with calibration data stored in a database, wherein the determining of the first laser energy output level is based on the correlating of the first data with the calibration data.

3. The method of claim 2, wherein the database is a local database.

4. The method of claim 2, wherein the database is a remote database.

5. The method of claim 1, wherein while the first probe emits the first energy from the excimer laser source at the first laser energy output level, the method further comprises performing a laser trabeculostomy on an eye of a patient.

6. A method comprising, upon each instance of connecting one of a plurality of excimer laser probes to an excimer laser source:
   receiving by a processor in communication with the excimer laser source, data from a readable device or label of the one of the plurality of excimer laser probes, wherein:
   the data is read automatically by a reader in communication with the processor;
   the data is indicative of at least a diameter of a fiber optic core of the one of the plurality of excimer laser probes;
   the excimer laser source is configured to generate laser energy to be provided to each of the plurality of excimer laser probes; and
   each of the plurality of excimer laser probes are single use and disposable, such that the plurality of excimer laser probes are each coupleable, one at a time, to the excimer laser source;
   determining, by the processor and based on the data, a laser energy output level to transmit to the one of the plurality of excimer laser probes connected to the excimer laser source; and
   transmitting, by the processor in response to receiving a first signal indicative of a user control of the excimer laser source, a second signal indicative of the laser energy output level to the excimer laser source, wherein the second signal is configured to cause the one of the plurality of excimer laser probes to emit energy from the excimer laser source at the laser energy output level.

7. The method of claim 6, further comprising, upon each instance of connecting the one of the plurality of excimer laser probes to the excimer laser source, correlating, by the processor, the data with calibration data stored in a local or remote database, wherein the determining of the laser energy output level is based on the correlating of the data with the calibration data.

8. The method of claim 7, wherein the calibration data comprises a range of possible diameters of the plurality of excimer laser probes and a range of corresponding laser energy output levels for each of the range of possible diameters.

9. The method of claim 7, wherein the calibration data comprises a plurality of sets of values, wherein each set of values comprises a desired laser energy output level and a corresponding diameter of the fiber optic core.

10. The method of claim 6, wherein while the one of the plurality of excimer laser probes emits the energy from the excimer laser source, the method further comprises performing a laser trabeculostomy on an eye of a patient.

11. The method of claim 6, wherein while the one of the plurality of excimer laser probes emits the energy from the excimer laser source, the method further comprises automatically adjusting, by the processor, the laser energy output level to maintain a desired laser energy output level.

12. The method of claim 6, wherein the data is received at the processor from the one of the plurality of excimer laser probes coupled to the excimer laser source prior to providing an operator with control over the excimer laser source.

13. The method of claim 6, wherein the data is received automatically by the reader upon connection of the one of the plurality of excimer laser probes to the excimer laser source.

14. The method of claim 6, wherein the one of the plurality of excimer laser probes connects to the excimer laser source by attaching a connection assembly of the one of the plurality of excimer laser probes to a connection port of the excimer laser source.

15. The method of claim 6, wherein while the one of the plurality of excimer laser probes is connected to the excimer laser source, the fiber optic core of the one of the plurality of excimer laser probes is optically connected to the excimer laser source.

16. The method of claim 6, wherein the determining of the laser energy output level by the processor further comprises transmitting, by the processor to a remote server on which a calibration database is stored, the data indicative of at least the diameter of the fiber optic core of the one of the plurality of excimer laser probes.

17. The method of claim 16, wherein the data is first data, and further wherein the determining of the laser energy output level by the processor further comprises receiving, at the processor after the transmitting of the data to the remote server, second data indicative of the laser energy output level from the remote server.

18. The method of claim 17, wherein the laser energy output level is determined by the processor based on the second data indicative of the laser energy output level from the remote server.

19. A system comprising:
a calibration database;
an excimer laser source;
a plurality of excimer laser probes;
a reader; and
a processor in communication with the calibration database and the reader, wherein the processor is configured to, upon each instance of one of the plurality of excimer laser probes connecting to excimer laser source:
receive data from a readable device or label of the one of the plurality of excimer laser probes, wherein:
the data is read automatically by the reader;
the data is indicative of at least a diameter of a fiber optic core of the one of the plurality of excimer laser probes;
the excimer laser source is configured to generate laser energy to be provided to each of the plurality of excimer laser probes; and
each of the plurality of excimer laser probes are single use and disposable, such that the plurality of excimer laser probes are each coupleable, one at a time, to the excimer laser source;
determine, based on the data, a laser energy output level to transmit to the one of the plurality of excimer laser probes connected to the excimer laser source; and
transmit, in response to receiving a first signal indicative of a user control of the excimer laser source, a second signal indicative of the laser energy output level to the excimer laser source, wherein the second signal is configured to cause the one of the plurality of excimer laser probes to emit energy from the excimer laser source at the laser energy output level.

20. The system of claim 19, wherein the calibration database is stored locally on a memory connected to the processor or the calibration database is stored remotely on a remote server in communication with the processor over a network.

* * * * *